United States Patent
Friedman (10) Patent No.: US 6,659,637 B2
(45) Date of Patent: Dec. 9, 2003

(54) VERTICAL ELECTROMAGNETIC SHAKER FOR BIOLOGICAL AND CHEMICAL SPECIMENS

(75) Inventor: Mitchell A. Friedman, Randallstown, MD (US)

(73) Assignee: Union Scientific Corporation, Randallstown, MD (US)

( * ) Notice: Subject to any disclaimer, the term of this patent is extended or adjusted under 35 U.S.C. 154(b) by 141 days.

(21) Appl. No.: 09/969,883

(22) Filed: Oct. 3, 2001

(65) Prior Publication Data

US 2002/0044495 A1 Apr. 18, 2002

Related U.S. Application Data

(60) Provisional application No. 60/237,587, filed on Oct. 3, 2000.

(51) Int. Cl.⁷ ................................................. B01F 11/00
(52) U.S. Cl. ....................... 366/212; 366/214; 366/110; 366/111
(58) Field of Search ................................. 366/111, 112, 366/110, 114, 127, 209, 217, 216, 212; 422/99, 104

(56) References Cited

U.S. PATENT DOCUMENTS

| | | | |
|---|---|---|---|
| 1,756,325 A | * | 4/1930 | Williams ..................... 366/114 |
| 2,198,637 A | | 4/1940 | Smith |
| 2,247,978 A | | 7/1941 | Van Arkel |
| 2,255,799 A | | 9/1941 | Meinzer |
| 2,356,004 A | * | 8/1944 | Price ........................... 366/110 |
| 2,895,064 A | | 7/1959 | Hoff et al. |
| 2,900,138 A | | 8/1959 | Strate |
| 3,108,408 A | | 10/1963 | Dahlquist et al. |
| 3,155,853 A | | 11/1964 | Spurlin |
| 3,310,292 A | | 3/1967 | Moore |
| 3,316,470 A | | 4/1967 | Scott |
| 3,601,372 A | | 8/1971 | Harmes, III |
| 3,635,446 A | | 1/1972 | Kurosawa et al. |
| 3,637,190 A | | 1/1972 | Isaacson |
| 3,769,758 A | | 11/1973 | McDonald |
| 3,876,379 A | | 4/1975 | Ghim |
| 3,978,623 A | | 9/1976 | Smith |
| 4,061,315 A | | 12/1977 | Eitzen et al. |
| 4,102,649 A | | 7/1978 | Sasaki |
| 4,118,801 A | | 10/1978 | Kraft et al. |
| 4,183,677 A | | 1/1980 | de Bruyne |
| 4,202,634 A | | 5/1980 | Kraft et al. |

(List continued on next page.)

Primary Examiner—Tony G. Soohoo
(74) Attorney, Agent, or Firm—Whiteford, Taylor & Preston LLP; Gregory M. Stone; Jeffrey C. Maynard (57) ABSTRACT

An electromagnetic vibratory microplate shaker is disclosed of simplified design and improved mixing capability over previously known microplate shaker devices, comprising an electromagnetic drive assembly mounted within a rigid base and operatively connected to a microplate support platform. The support platform is in turn supported by a plurality of horizontally arrayed leaf springs. During operation, an electromagnet is rapidly energized and de-energized causing an armature of the drive assembly to be pulled in and released up to 7,200 times per minute, in turn imparting a vertical reciprocating vibration to the support platform and the microplates or multi-tube racks held thereon. Means are provided for adjusting the amplitude of the vibration as necessary to enable the entire volume of liquid within each microplate well or tube to be vertically displaced within the well or tube during each vibration cycle, thus ensuring thorough mixing of the contents of each microplate well or tube irrespective of its diameter, while keeping suspended solids truly suspended during the mixing cycle. Also provided is a static indicia of amplitude of vibration fixedly mounted on the support platform to enable the user to determine the optimal vibrational amplitude to use for a particular series of microplates or multi-tube racks being vibrated.

25 Claims, 4 Drawing Sheets

U.S. PATENT DOCUMENTS

| | | |
|---|---|---|
| 4,264,559 A | 4/1981 | Price |
| 4,305,668 A | 12/1981 | Bilbrey |
| 4,356,911 A | 11/1982 | Brown |
| 4,422,768 A | 12/1983 | Solomon |
| 4,610,546 A | 9/1986 | Intraub |
| 4,702,610 A | 10/1987 | Reynolds, Jr. |
| 4,870,982 A | 10/1989 | Liu |
| 5,060,151 A | 10/1991 | Mikyska et al. |
| 5,153,136 A | 10/1992 | Vandenburgh |
| 5,427,451 A | 6/1995 | Schmidt |
| 5,593,228 A | 1/1997 | Tannenbaum |
| 5,608,693 A | 3/1997 | Richards |
| 5,821,657 A | 10/1998 | Falconer et al. |
| 5,921,477 A | 7/1999 | Tomes et al. |
| 6,508,582 B2 * | 1/2003 | Friedman .................... 366/110 |

* cited by examiner

This is the smallest flask that will work well with orbit diameter shown

Orbit dia. of center of large flask

Orbit dia. of every point on this platform

Most of the centrifugal forces on the liquid are now contained within the flask and will reverse every 180° insuring adequate mixing

LARGE BEAKER OR FLASK

The mixing currents are entirely inside the vial and mixing the contents occurs.

(Prior Art)

FIGURE 1b

Vial is smaller than orbit diameter

Orbit diameter of the center of small vial and path of motion

Orbit dia. of every point on this platform

Centrifugal force pushes liquid to outer wall of vial

Contents do not mix (Prior Art)

VERTICAL ELECTROMAGNETIC SHAKER FOR BIOLOGICAL AND CHEMICAL SPECIMENS

CROSS-REFERENCE TO RELATED APPLICATIONS

The present application is based upon and gains priority from U.S. Provisional Patent Application Ser. No. 60/237,587, filed Oct. 3, 2000 by the inventor herein and entitled "Vertical Electromagnetic Shaker for Biological and Chemical Specimens," the specification of which is incorporated herein by reference.

BACKGROUND OF THE INVENTION

1. Field of the Invention

The invention disclosed herein relates generally to shakers for microplates, small diameter test tubes, and like-configured fluid containers, and more particularly to an electromagnetic vibratory microplate and multi-tube rack shaker of simplified construction for imparting vertical vibration to one or more microplates or multi-tube racks containing a multitude of biological or chemical samples, such vertical vibration being of sufficient amplitude to cause effective and thorough mixing of the contents of each microplate well or tube.

2. Description of the Background

The processing of biological specimens or chemical products in laboratories often requires the mixing of analytes within a container in order to carry out a desired reaction. Such containers have often comprised beakers or flasks whose contents were traditionally mixed by either manually shaking the beaker or flask, or using a stirring rod. Other mixing apparatus have included a Teflon coated magnet placed within a beaker or flask and driven magnetically in a rotary motion to mix the beaker or flask contents. Unfortunately, manually shaking the beaker or flask provides insufficient means to control the mixing of the contents and easily results in laboratory technicians accidentally dropping the container and ruining the sample. Likewise, the use of stirring rods has required that the laboratory technician either thoroughly wash the rod between specimens in order to avoid cross-contamination, or throw away and replace disposable rods for applications with large numbers of specimens, making the rapid mixing of large numbers of specimens highly impractical.

Figure 1A:
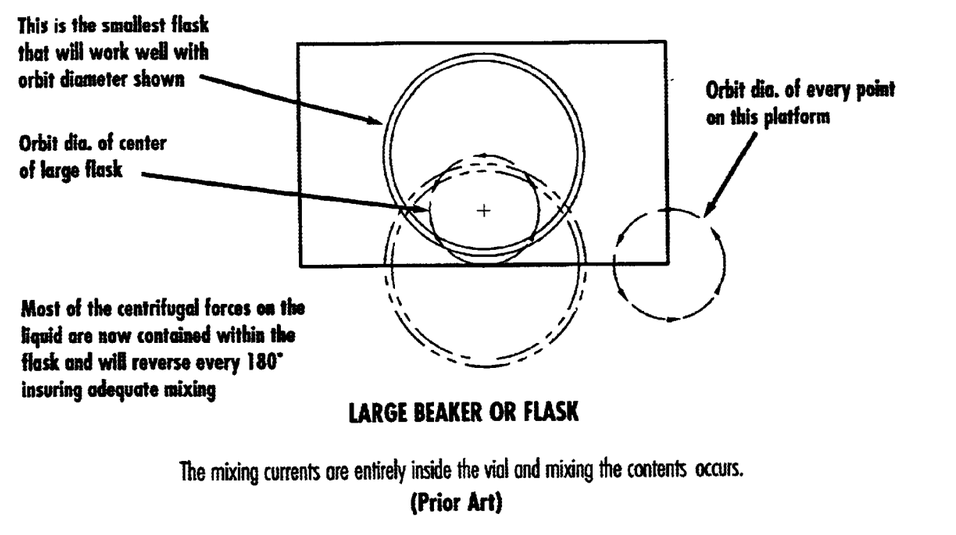
FIG. 1a is a top-down schematic view of a prior art orbital specimen shaker.

In order to overcome these shortcomings, motor driven orbital shakers were developed which enabled a laboratory technician to place a beaker or flask on a motor driven platform that would cause the beaker or flask to travel in a continuous orbit to mix its contents. So long as the diameter of the beaker or flask holding a sample is greater than the orbit diameter of the platform, mixing of the contents will occur. For example, as shown in the schematic view of a prior art orbital mixer of FIG. 1a, the center of the flask travels in an orbital path equivalent to the orbit of the platform, and the centrifugal forces on the liquid will reverse every 180° to provide adequate mixing of the contents.

Figure 1B:
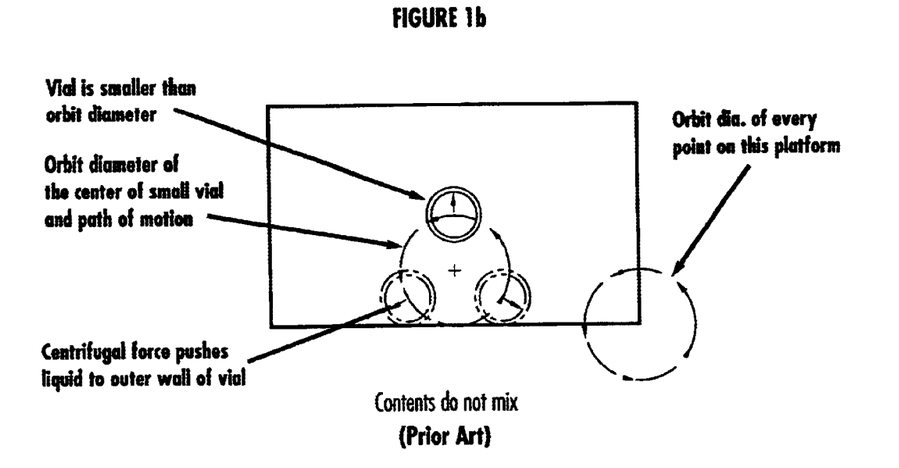
FIG. 1b is a second top-down schematic view of a prior art orbital specimen shaker.

However, as the number of specimens needed to be analyzed in a given time period has grown, the quest for efficiency in the processing of such specimens has resulted in smaller and smaller sample sizes being studied, and thus smaller and smaller containers for holding those samples. Unfortunately, as smaller sized beakers and flasks were used, those orbital shakers having an orbit diameter that was larger than the beaker or flask diameter were shown to be ineffective for mixing the contents. For example, as shown in the schematic view of a prior art orbital mixer of FIG. 1b, a beaker or flask having a diameter that is smaller than the orbit diameter of the mixer simply travels in the shaker's orbit, and centrifugal forces drive the liquid contained within the beaker or flask against the side of the container which is furthest from the center of orbit. If there are any suspended solids in the liquid, they will likewise be driven against the outside wall of the container, and fail to mix with the solution. In order to alleviate this problem, a few orbital shakers have been made available having orbit diameters of as little as $\frac{1}{8}$".

As the need for processing greater numbers of samples in shorter amounts of time continued to grow, microplates were developed to hold multiple samples of a chemical or biological material to be analyzed in a single, compact structure having a rectangular grid of a large number of distinct "wells." Such microplates are available today in 96-well, 384-well, and even 1536-well configurations. Likewise, racks of small diameter tubes have been developed providing a similar array of specimen-holding chambers. Such tube racks are available in up to 96-tube configurations. Obviously, the greater the number of wells or tubes in a standard microplate or rack footprint, the smaller the diameter of the well or tube, such that for microplates and tubes having chamber diameters of far less than $\frac{1}{8}$", an orbit of far less than $\frac{1}{8}$" would likewise be required in order to ensure proper mixing. As was true with orbital mixers for large flasks, the contents of such a small diameter tube rotating in an orbit larger than its own diameter are difficult to mix. Using an orbit larger than the well or tube diameter causes the liquid contents to move to the outside of the orbit and rise up the inner wall of the tube which is closest to the outside radius of the orbit. The contents of the tube begin to spin inside the tube with a relatively small amount of relative motion (or shearing) between adjacent layers of fluid within the walls of the tube. As the orbital speed is increased, the liquid in the tube is forced outward by centrifugal force, rising up the inner wall of the tube until it spills over the top. Given the orbit diameter limitation of only $\frac{1}{8}$", traditional horizontal orbital shakers have thus been ineffective in shaking microplates and tube collections having such small diameter chambers.

Given the failure of traditional orbiting mixing apparatus to provide an effective means of mixing the contents of small well microplates and small diameter tubes, attempts have been made to provide mixing apparatus specifically configured for mixing the contents of microplate wells, but unfortunately have also met with little success. For example, U.S. Pat. No. 3,635,446 to Kurosawa et al. discloses a microplate shaking device using an eccentric motor to uncontrollably vibrate a microplate holding plate through a horizontal plane. Likewise, U.S. Pat. No. 4,102,649 to Sasaki discloses a microplate shaker device which pivotally mounts a microplate to a vibration plate, and slidably mounts the microplate atop a number of props. The vibration plate is caused to vibrate by either an electromagnet or an eccentric wheel in a nonlinear, horizontal manner. Further, U.S. Pat. No. 4,264,559 to Price discloses a mixing device for a specimen holder comprising two springlike metal rods upon which a specimen holder is mounted, the rods being fixed at one end in a vertical block, and a weight positioned adjacent the opposite end of the rods. Manually plucking one of the rods imparts a "pendulum-like" vibration to both rods, and thus to the specimen holder. Finally, U.S. Pat. No. 5,921,477 to Tomes et al. discloses an agitating apparatus for a "well plate holder" which comprises a vertically-oriented reciprocating saw as a means for vertically shaking a multi-well plate, and provides agitating members comprising small diameter copper or stainless steel balls within each well.

Unfortunately, none of the known prior art devices have been able to provide controlled, vertical vibration to a microplate or collection of small diameter tubes in order to create vertical vibrational motion of sufficient turbulence to thoroughly mix the well or tube contents.

Furthermore, U.S. Pat. No. 5,427,451 to Schmidt discloses a mixer which utilizes a complex, microprocessor-controlled circuit to provide oscillatory drives comprised of permanent magnets and drive coils juxtaposed therewith, with each coil being independently energized by separate variable frequency sources. The drive circuits are configured to alternately attract and repel the permanent magnets so as to provide the oscillatory motion, thus requiring actuation of the drive coils at all times during operation of the mixer. Such a construction is highly complex, requiring precise control of the timing of each drive cycle, and exhibits high energy requirements for its operation. It would be highly advantageous to provide a simplified mixing construction that has a lower energy requirement, but that can still provide consistent, reliable mixing through linear vibration of test specimen containers.

It would therefore be advantageous to provide an electromagnetic, linear shaker of simplified construction which will ensure the efficient linear vibrational mixing of the contents of microplates and small diameter tubes, while keeping suspended solids truly suspended during the mixing cycle.

SUMMARY OF THE INVENTION

It is, therefore, an object of the present invention to provide a microplate and multi-tube rack shaker which avoids the disadvantages of the prior art.

It is another object of the present invention to provide a microplate and multi-tube rack shaker which can efficiently mix the contents of microplates and specimen tubes of all sizes while keeping suspended solids truly suspended during the mixing cycle.

It is yet another object of the present invention to provide a microplate and multi-tube rack shaker which enables the contents of a microplate and specimen tube to be properly mixed in a shorter amount of time than has been previously performed by prior art devices.

It is still yet another object of the present invention to provide a microplate and multi-tube rack shaker which enables the effective mixing of the contents of a plurality of microplates and multi-tube racks during a single mixing process.

It is even yet another object of the present invention to provide a microplate and multi-tube rack shaker of simplified design over prior art devices which ensures thorough mixing of the well and tube contents irrespective of the diameter of the wells and tubes.

It is still yet another object of the present invention to provide a microplate and multi-tube rack shaker of a more compact size than has been previously available in prior art shakers to enable such a shaker to be readily placed within a refrigerator or incubator for temperature-sensitive mixing applications.

It is even yet another object of the present invention to provide a microplate and multi-tube rack shaker of simplified construction that provides thorough mixing of the microplate contents through vibration directed solely in the vertical direction.

It is still even yet another object of the present invention to provide a microplate and multi-tube rack shaker which consistently applies a controlled vertical vibration to the contents of the microplate wells or tubes so as to create sufficient turbulence within each well or tube to ensure adequate mixing.

It is still even yet another object of the present invention to provide a microplate and multi-tube rack shaker having means for adjusting the amplitude of vibration to a sufficient level to vertically displace the entire contents of each well and tube during each vibration cycle.

It is still even yet another object of the present invention to provide a microplate and multi-tube rack shaker having a static indicia of amplitude of vibration attached to a microplate or multi-tube rack support tray on the shaker.

In accordance with the above objects, an electromagnetic vibratory microplate and multi-tube rack shaker is disclosed of simplified design and improved mixing capability over previously known shaker devices. The electromagnetic vibratory microplate and multi-tube rack shaker of the instant invention comprises an electromagnetic drive assembly vertically mounted within a rigid base and operatively connected to a microplate and multi-tube rack support platform. The support platform is in turn resiliently supported by a plurality of horizontally arrayed leaf springs. During operation, the electromagnet is rapidly energized and de-energized causing an armature of the drive assembly to be pulled in and released up to 7,200 times per minute, in turn deflecting the leaf springs in the vertical direction and imparting a reciprocating vertical vibration to the support platform and the microplates or multi-tube racks held thereon. Means are provided for adjusting the amplitude of the vibration as necessary to enable the entire volume of liquid within each well or tube to be vertically displaced within the well or tube during each vibration cycle, thus ensuring thorough mixing of the contents of each well or tube irrespective of its diameter, while keeping suspended solids truly suspended during the mixing cycle. Also provided is a static indicia of amplitude of vibration fixedly mounted on the support platform to enable the user to determine the optimal vibrational amplitude to use for a particular series of microplates or multi-tube racks being vibrated.

It should also be noted that the leaf spring members are entirely responsible for moving the support platform in the reverse direction from which it is driven by the electromagnet. Thus, the electromagnet need only be energized during half of each vibration cycle, thus eliminating the need for a permanent magnet within the drive assembly and reducing the energy required to operate the assembly.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

In large diameter test tubes (such as is evident with a standard 10 ml test tube), mixing of the tube contents may be achieved by applying circular or rotational driving forces to the tube, in turn allowing the liquid contents to swirl around the center of the tube. However, in a tube four times smaller, the adhesion of the liquid to the walls of the tube leaves very little liquid left in the middle of the tube to move around. In order to effectively mix liquids in such a tube, the liquids must move relative to one another. Thus, mixing of fluids in long, narrow wells, such as fluid columns in small diameter test tubes, must be achieved by shaking the tube up and down so that the momentum of all of the liquid can be used to make the liquid move.

As the vertical vibratory motion seeks to move the liquid (and the small diameter test tube in which it is stored) up and down, the attraction of the molecules of the liquid to each other on the surface of the liquid and gas interface tend to hold the liquid in place with respect to the walls of the small diameter tube. The molecules of liquid are less attracted to the molecules of gas than they are to one another. The unbalance of force under the entire surface of the liquid creates a relative higher pressure in the liquid. The attraction of molecules side by side on the surface is called surface tension, and is usually constant for a given liquid and temperature. The pressure that develops in the liquid will eventually be balanced by the forces holding the molecules on the surface together. This pressure is proportional to the surface tension, and is inversely proportional to the radius of the tube. In turn, the force developed by the surface tension that must be overcome in order to move the volume of liquid (and thus achieve effective mixing) is directly proportional to the radius of the tube. For a given amplitude and frequency of vibration, there is a tube diameter below which the inertial forces of the volume of liquid in the tube will be insufficient to overcome the force caused by the surface tension of the liquid, such that no movement or mixing will occur.

Figure 1C:
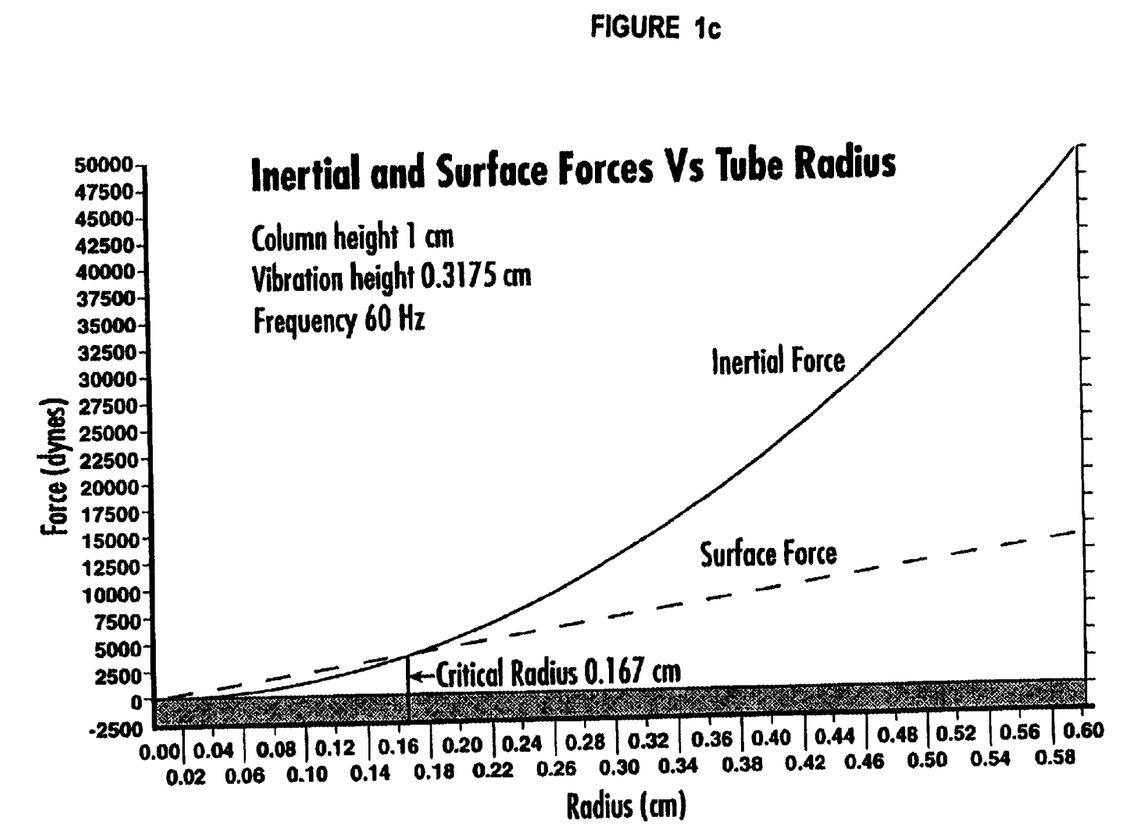
FIG. 1c is a plot of vertical inertial force and surface tension of a fluid versus the radius of a round tube in which such fluid is held and vertically shaken.

FIG. 1c is a plot of vertical inertial force and surface tension force versus the radius of a round tube (using cgs units), at 20° C., a liquid column height l=1 cm, height of vibration h=0.3175 cm, and frequency in the vertical direction f=60 Hz. Most important, the two curves cross at a critical radius, where the vertical inertial force and surface tension force are equal. Remaining above this critical radius will allow the inertial forces generated by the vertical vibration of the tube contents to cause thorough mixing of those contents.

It should be noted that the inertial force necessary to achieve mixing in a narrow tube is affected by several factors, including the liquid column height, the radius of the tube, the frequency of vibration, and the amplitude of vibration. A system providing for the mixing of fluids in deep wells should therefore account for such factors so that particular adjustments can be made for a given system.

Figure 2:
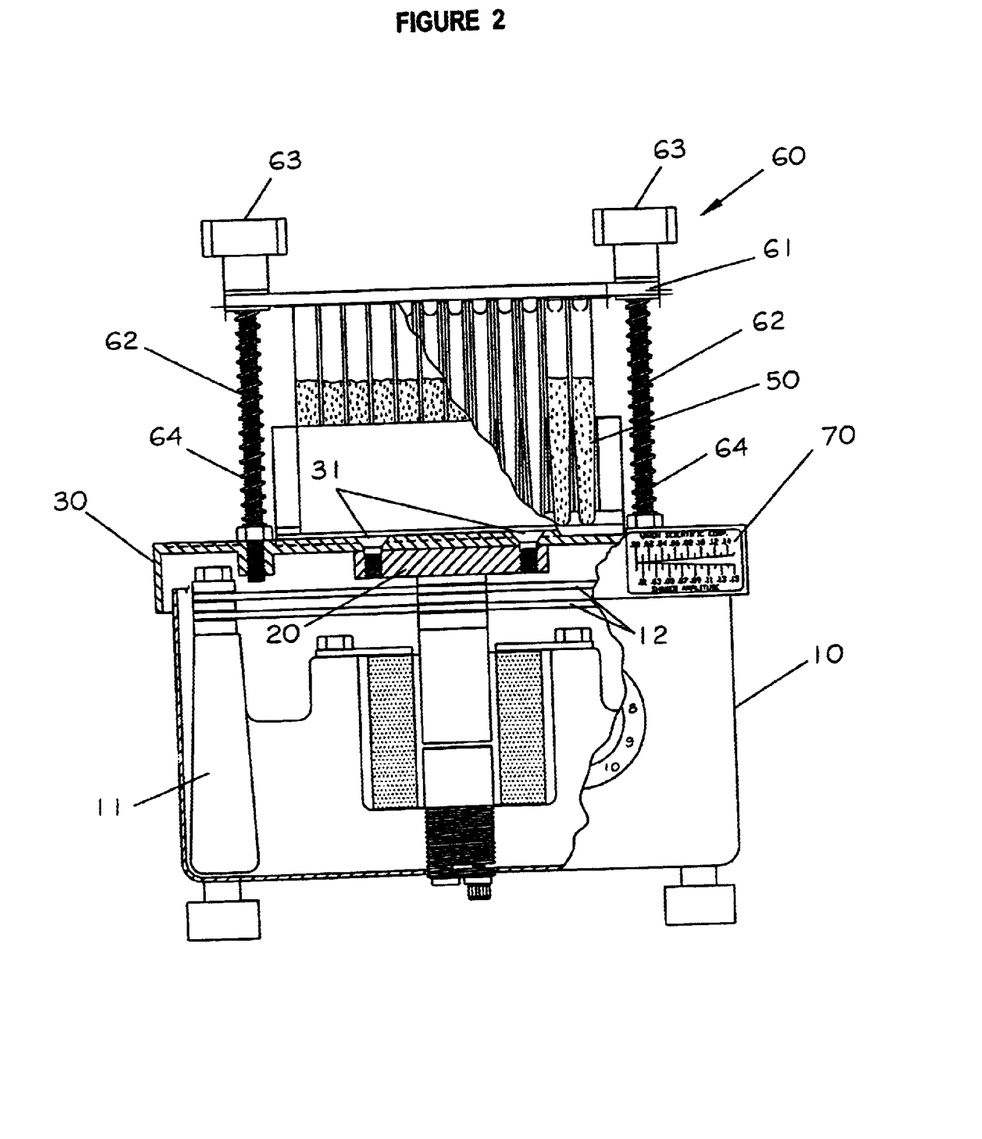
FIG. 2 is a side, partial sectional view of the electromagnetic vibratory microplate and multi-tube rack shaker of the instant invention.

Thus, in order to provide an apparatus capable of effectively mixing both shallow well microplates and deep, narrow fluid well multi-tube racks, as shown in the side view of FIG. 2, the instant invention comprises a base unit (shown generally at 10), a mounting block 20, and a microplate and multi-tube rack support plate 30. An electromagnetic drive mechanism 11 is vertically mounted within base unit 10 and is operatively connected to mounting block 20 to impart vertical vibratory motion to mounting block 20. Mounting block 20 is likewise supported above a plurality of horizontally arrayed leaf springs 12, leaf springs 12 serving to bias mounting block 20 to an at-rest position. As will be described in greater detail below, electromagnetic drive mechanism 11 and leaf springs 12 work in combination to impart a cyclical vertical vibration to microplate and multi-tube rack support plate 30.

Electromagnetic drive mechanism 11 is vertically mounted within base unit 10. As shown more particularly in the detailed sectional view of base unit 10 of FIG. 3, the drive mechanism comprises a coil 40 surrounding a core assembly 41 which is rigidly attached to the base housing. An armature assembly 42 is positioned opposite core 41 a sufficient distance to define an air gap 43 between the core assembly and the armature. Armature 42 is in turn rigidly attached to mounting block 20 via threaded member 44.

Figure 3:
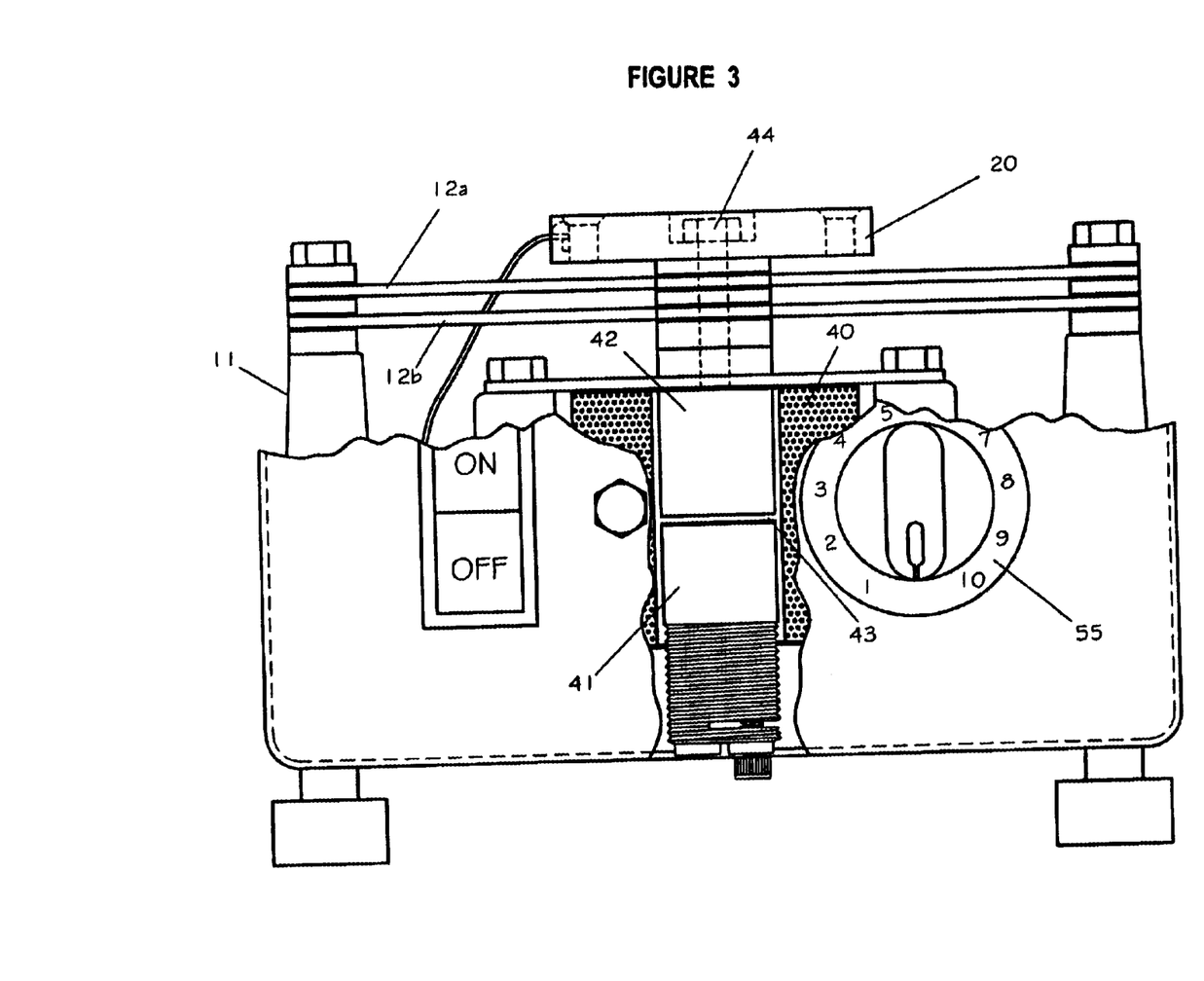
FIG. 3 is a detailed sectional view of base 10.

Positioned between mounting block 20 and armature 42 are a plurality of horizontally aligned leaf springs 12a and 12b. Leaf springs 12 are fixed at opposing ends of base unit 10, and are separated from one another using spacers.

The above-described base assembly and electromagnetic drive are known to those of ordinary skill in the art, and are readily commercially available.

In use, a rectified current sine wave is applied to coil 40, thus energizing the coil for half of a cycle and de-energizing the coil for the remainder of the cycle. When coil 40 is energized, core assembly 41 is magnetized and attracts armature assembly 42. As armature assembly 42 moves towards core assembly 41, it pulls mounting block 20 down against the bias of leaf springs 12, in turn flexing leaf springs 12. When coil 40 is de-energized, the magnetic pull between core assembly 41 and armature assembly 43 is released, and leaf springs 12 return to and pass through their at rest position, in turn pushing mounting block 20 upward. This cycle continues as long as power is supplied to the electromagnetic drive means 11 such that mounting block 20 and microplate support plate 30 are vibrated in a strictly vertical direction. During operation, the amplitude of the vibration is increased using control knob 55 until the amplitude of the vertical vibration becomes sufficient to vertically displace the entire volume of liquid within each well or tube during each vibration cycle, thus ensuring thorough mixing of the contents of each well or tube irrespective of its diameter, while keeping suspended solids truly suspended during the mixing cycle.

As seen more particularly in FIG. 2, a static indicia 70 is affixed to the sidewall of microplate and multi-tube rack support plate 30. During operation, static indicia 70 vibrates at the same magnitude as support plate 30. As static indicia 70 vibrates, an operator viewing the vibratory static indicia 70 is in turn presented an indication of the magnitude of vibration of the entire microplate support plate 30. Thus, for a given collection of microplates or multi-tube racks all having the same volume of samples to be vibrated, a user need only adjust the vibrational amplitude during mixing of the first microplate or multi-tube rack in the collection to a level that is sufficient to vertically displace the entire volume of each well or tube to in turn provide for rapid and thorough mixing of the well or tube contents. Thereafter, the user may simply turn off the shaker, remove the processed microplate or rack and insert a microplate or rack holding unmixed samples, and turn the shaker back on at the proper magnitude for that microplate or multi-tube rack collection. This greatly simplifies the mixing process for the user and enables faster, more efficient processing of the collection.

The electromagnetic drive 11 of the instant invention is capable of the rapid vibration of a microplate or multi-tube rack with a frequency of up to 7,200 vibrations per minute. Such rapid vibration within a relatively small displacement of the microplate or multi-tube rack vastly improves both the control of the mixing operation, allowing rapid vibrations without risking stability of the microplates or racks mounted on support plate 30, and the economy of carrying out such mixing operations by shortening the amount of time a sample need be processed under an increased vibrational frequency.

Referring again to FIG. 2, mounting block 20 is rigidly attached to a microplate support plate 30 via threaded members 31. Microplate support plate 30 is preferably provided on its upper face with one or more indentations (not shown) dimensioned slightly larger than the footprint of a standard microplate, or a multi-tube rack, both of which are readily commercially available from numerous laboratory supply facilities. The indentations of support plate 30 provide a nesting pocket to receive a microplate or multi-tube rack, the side walls of the indentations preventing the sideways movement of the microplate or multi-tube rack in any direction during operation. To further ensure that the microplates or tube racks remain affixed to the support plate during operation of the shaker, a clamping assembly (shown generally at 60) is provided. Clamping assembly 60 includes a horizontally aligned clamping plate 61 mounted on opposing vertical rods 62. The top of each vertical-rod 62 is provided a knob 63, while the bottom of each rod 62 is threadably mounted within support plate 30. Spring biasing members 64 are positioned between support plate 30 and clamping plate 61 to upwardly bias clamping plate 61 against knobs 63 when the shaker is not in use. When the shaker is in use and one or more microplates or multi-tube racks are positioned on support plate 30, knobs 63 may be rotated in order to push clamping plate 61 down (against the bias of biasing members 64) until clamping plate 61 comes into contact with the top face of a microplate or the top end of one or more tubes held within multi-tube rack 50. At this point, knobs 63 may be tightened, thus providing a clamp-down force on the top face of microplate or multi-tube rack 50 to hold it firmly in place during operation of the shaker. By enabling multiple microplates and multi-tube racks to be mounted on a single shaker device during a shaking or mixing operation, and thus the simultaneous mixing of those multiple microplates and multi-tube trays, even greater testing economies are achieved than have been previously available in prior art devices.

As may be seen in FIG. 2, the simplicity of the driving mechanism of the shaker of the instant invention enables a shaker having greater ability to control a mixing or shaking operation in a shorter amount of time than previously known devices, but whose dimensional footprint remains significantly less than traditional shaker devices. Such compact and simplified construction thus allows the shaker and any microplates or multi-tube racks mounted thereon to be easily placed within a refrigerator or incubator for shaking or mixing operations that require temperature conditioning.

While the apparatus of the instant invention is disclosed as functioning for its primary purpose to provide vertical vibration to one or more microplates or one or more multi-tube racks in order to mix the contents held therein, it should be noted that the apparatus may also be used to mix the contents of even a single tube held with a rack and positioned between support plate 30 and clamping plate 61.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

I claim:

1. A vertical electromagnetic shaker for biological and chemical specimens comprising:

a base;

a drive means mounted within said base;

a microplate and multi-tube rack support tray operatively attached to said drive means so as to translate only in a generally vertical direction in response to actuation of said drive means, and configured to hold at least one microplate or multi-tube rack thereon, said drive means being configured to direct only an upward, generally vertical vibration component to said microplate and multi-tube rack support tray; and biasing members operatively attached to said support tray, said biasing members directing a downward, generally vertical vibration component to said support tray and biasing said support tray to an at-rest position.

2. The vertical electromagnetic shaker of claim 1, wherein said drive means further comprises an electromagnetic drive unit vertically mounted within said base so as to generate a vibrational force in a direction that is generally at a right angle to said support tray.

3. The vertical electromagnetic shaker of claim 1, said support tray further comprising:

a generally horizontal tray having at least one indentation configured to receive at least one microplate or multi-tube rack.

4. The vertical electromagnetic shaker of claim 3, said indentation being defined by a shallow rectangular well having dimensions generally corresponding to a bottom face of a microplate or multi-tube rack.

5. The vertical electromagnetic shaker of claim 3, said support tray further comprising means for preventing movement of said at least one microplate or multi-tube rack with respect to said support tray.

6. The vertical electromagnetic shaker of claim 5, said means for preventing movement of said at least one microplate or multi-tube rack further comprising a clamp configured for holding a portion of a bottom face of said microplate or multi-tube rack against said at least one indentation.

7. The vertical electromagnetic shaker of claim 6, said clamp further comprising:

at least one rod extending generally vertically upward from said support plate;

a vertically translatable knob operatively connected to each said at least one vertical rod;

a clamping plate slidably mounted on said at least one vertical rod below said knob; and biasing means upwardly biasing said clamping plate against said knob.

8. A vertical electromagnetic shaker for biological and chemical specimens comprising:

a microplate and multi-tube rack support tray;

means for directing only an upward, generally vertical vibration component to said microplate and multi-tube rack support tray; and biasing means directing a downward, generally vertical vibration component to said support tray.

9. The vertical electromagnetic shaker of claim 8, said means for directing only an upward, generally vertical vibration component to said support tray further comprising:
 an electromagnetic drive unit; and
 a mounting block affixed to said electromagnetic drive unit so as to receive said upward, generally vertical vibration component generated therefrom, and affixed to said microplate support tray for translating said upward, generally vertical vibration component thereto.

10. The vertical electromagnetic shaker of claim 9, said biasing means further comprising a plurality of resilient members biasing said mounting block and said support tray to an at-rest position.

11. The vertical electromagnetic shaker of claim 10, wherein said plurality of resilient members comprise leaf springs.

12. The vertical electromagnetic shaker of claim 11, wherein said leaf springs are mounted in a generally horizontal position so as to provide bias against movement of said support tray in a generally vertical direction.

13. A vertical electromagnetic shaker for biological and chemical specimens comprising:
 a base;
 an electromagnetic drive vertically mounted within said base;
 a microplate and multi-tube rack support tray operatively connected to said electromagnetic drive and mounted for movement only in a generally vertical reciprocating oscillation, said drive means being configured to direct only an upward, generally vertical vibration component to said microplate and multi-tube rack support tray; and
 a plurality of spring members directing a downward, generally vertical vibration component to said support tray and biasing said support tray to an at-rest position.

14. The vertical electromagnetic shaker of claim 13, said support tray further comprising an upper face provided with an indentation dimensioned approximately equivalent to a footprint of a standard microplate or multi-tube rack.

15. The vertical electromagnetic shaker of claim 14, said indentation having a plurality of sidewalk of sufficient depth to prevent sideways movement of a microplate or multi-tube rack placed therein.

16. The vertical electromagnetic shaker of claim 13, said spring members further comprising a plurality of horizontally arrayed leaf springs.

17. The vertical electromagnetic shaker of claim 13, further comprising a mounting block disposed between said electromagnetic drive and said support tray.

18. The vertical electromagnetic shaker of claim 17, wherein said support tray is removably attached to said mounting block via at least one threaded connecting member.

19. The vertical electromagnetic shaker of claim 13, further comprising a static indicia of magnitude of vibration of the shaker.

20. The vertical electromagnetic shaker of claim 13, further comprising means for adjusting the amplitude of vibration imparted by said electromagnetic drive to said support tray.

21. The vertical electromagnetic shaker of claim 13, wherein said electromagnetic drive and said spring members work in combination to impart a cyclical vertical vibration to said support tray.

22. The vertical electromagnetic shaker of claim 13, said electromagnetic drive further comprising:
 a coil surrounding a magnetizable core assembly, said core assembly being rigidly affixed to said base; and
 an armature assembly opposite said core assembly and rigidly attached to said support tray;
 wherein said spring members are mounted between said support tray and said armature assembly.

23. The vertical electromagnetic shaker of claim 13, further comprising means for preventing movement of said at least one microplate or multi-tube rack with respect to said support tray.

24. The vertical electromagnetic shaker of claim 23, said means for preventing movement of said at least one microplate or multi-tube rack further comprising a clamp configured for holding a portion of a bottom face of said microplate or multi-tube rack against said support tray.

25. The vertical electromagnetic shaker of claim 24, said clamp further comprising:
 at least one rod extending generally vertically upward from said support plate;
 a vertically translatable knob operatively connected to each said at least one vertical rod;
 a clamping plate slidably mounted on said at least one vertical rod below said knob; and
 biasing means upwardly biasing said clamping plate against said knob.

* * * * *